United States Patent [19]
Streicher et al.

[11] Patent Number: 5,905,182
[45] Date of Patent: May 18, 1999

[54] PROCESS FOR THE PURIFICATION OF BENZENE THAT COMPRISES TWO PERMEATION STAGES

[75] Inventors: Christian Streicher; Isabelle Prevost, both of Rueil Malmaison, France

[73] Assignee: Institut Francais Du Petrole, France

[21] Appl. No.: 08/936,099

[22] Filed: Sep. 23, 1997

[30] Foreign Application Priority Data

Sep. 24, 1996 [FR] France ................... 96/11695

[51] Int. Cl.⁶ ................ C07C 7/144; C07C 7/04
[52] U.S. Cl. ............ 585/804; 585/818; 585/819
[58] Field of Search ................. 585/804, 818, 585/819, 805, 806

[56] References Cited

U.S. PATENT DOCUMENTS

| | | | |
|---|---|---|---|
| 2,923,749 | 2/1960 | Lee et al. | 585/819 |
| 2,947,687 | 8/1960 | Lee | 585/818 |
| 2,970,106 | 1/1961 | Binning et al. | 208/347 |
| 2,985,588 | 5/1961 | Binning et al. | 585/819 |
| 3,043,891 | 7/1962 | Stuckey | 585/819 |
| 3,062,905 | 11/1962 | Jennings et al. | 585/818 |
| 4,748,288 | 5/1988 | Bitter et al. | 585/818 |
| 4,892,564 | 1/1990 | Cooley | 55/16 |
| 4,944,880 | 7/1990 | Ho et al. | 210/640 |
| 4,962,270 | 10/1990 | Feimer et al. | 585/819 |
| 4,997,906 | 3/1991 | Thaler et al. | 528/272 |
| 5,019,666 | 5/1991 | Sartori et al. | 585/819 |
| 5,396,019 | 3/1995 | Sartori et al. | 585/819 |

FOREIGN PATENT DOCUMENTS

| | | |
|---|---|---|
| 952 102 | 3/1964 | United Kingdom . |
| 2 268 186 | 1/1994 | United Kingdom . |

*Primary Examiner*—Walter D. Griffin
*Attorney, Agent, or Firm*—Millen, White, Zelano & Branigan, P.C.

[57] ABSTRACT

A mixture that contains benzene, other aromatic hydrocarbons and paraffinic hydrocarbons and/or naphthenic hydrocarbons that have 5 to 10 carbon atoms undergoes distillation in a first column, producing a distillate and a residue; a phase is drawn off laterally from the first distillation column, preferably at a point on the column where the benzene content is essentially at maximum where the toluene content is low; the phase that is drawn off is sent toward a first permeation stage, which produces a permeate that is enriched with benzene and a retentate; at least a portion of said retentate is recycled toward said first distillation column; the benzene-enriched permeate from stage (3) is sent to a second distillation column, from which the purified benzene comes out at the bottom and a distillate vapor comes out at the top; the distillate vapor is condensed, and the condensed distillate is sent at least in part to a second permeation stage; in said second permeation stage, a permeate that is also enriched in benzene and a retentate are separated; the permeate is recycled to the second distillation column; and the retentate is recycled toward the inlet of the first permeation stage or directly toward the first distillation column.

24 Claims, 1 Drawing Sheet

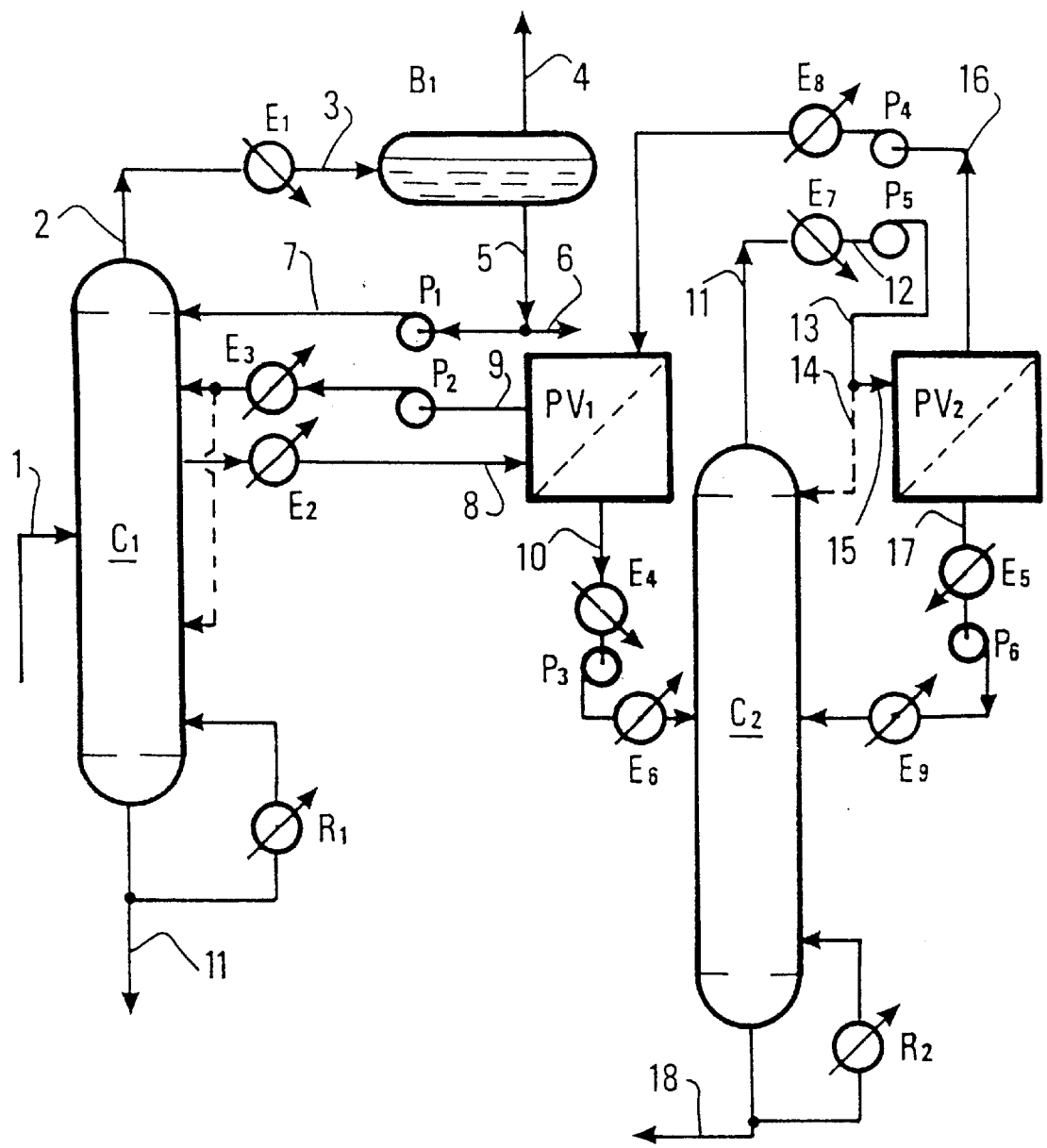

PROCESS FOR THE PURIFICATION OF BENZENE THAT COMPRISES TWO PERMEATION STAGES

FIELD OF THE INVENTION

This invention relates to a process for obtaining high-purity benzene that can be used particularly as a petrochemical base. It relates more particularly to a process for the purification of benzene from mixtures of hydrocarbons, whereby this process employs two permeation stages.

BACKGROUND OF THE INVENTION

Pure benzene can be obtained particularly by solvent extraction or by extractive distillation of the top effluents from naphtha-pre-fractionating columns before reforming or from columns used for post-fractionating catalytic reforming effluents.

It is known that, to reduce the benzene content of fuels, refiners use pre-fractionation of naphthas before reforming or post-fractionation of reforming effluents. Pre-fractionation makes it possible to eliminate a large portion of the benzene and its precursors (paraffins and naphthenes) at the top of the distillation and to obtain, at the bottom, a $C_{7+}$ fraction that feeds the reforming. Post-fractionation also makes it possible to obtain at the top of the column a light benzene-rich fraction and, at the bottom, a $C_{7+}$ fraction that feeds the fuel pool.

Benzene is present in these top effluents at relatively low concentrations, for example, 0 to 5% in the pre-fractionating elements and 1 to 10% in the post-fractionating effluents. Because of the small difference in volatility between these hydrocarbon batches and the other components of $C_5$ to $C_7$, it is difficult to separate benzene by simple distillation between the light components at the top and the heavy components at the bottom.

Only processes that use a selective solvent make it possible to obtain benzene with a purity of 99.9% by weight, which is required if it is to be used as a petrochemical base.

Thus, the processes most commonly used for purification of benzene are extractive distillation and solvent extraction. The difference between the two processes depends on the physico-chemical characteristics of the solvent that is used relative to those of benzene and consequently the method for regenerating the solvent.

These different treatments are disadvantaged, however, because of the low benzene content of the effluents that are obtained at the top of pre-fractionating columns or post-fractionating columns, which necessitates the use of large quantities of solvent.

One way of obtaining an effluent that is more concentrated in benzene and, consequently, of reducing the flow of solvent optionally required to extract the benzene is to carry out lateral drawing-off on the pre-fractionating column or post-fractionating column at the level where benzene concentration exhibits a peak. The benzene contents of such drawing-off do not exceed 10 to 30%, however.

SUMMARY OF THE INVENTION

This invention proposes a process which uses particularly the increase in benzene content from the draw-off provided by the use of a permeation stage. It is recalled that permeation is a separation technique that uses the difference in chemical potential that exists for each component on the two sides of a membrane. The flow that goes through the membrane is referred to as the "permeate," and the flow that does not go through the membrane is referred to as the "retentate." There are different permeation techniques for separating homogeneous mixtures, such as reverse osmosis, vapor permeation, and pervaporation.

The purpose of the process according to this invention is to obtain high-purity benzene, and the process also contributes to the production of fuel with a high octane number and low benzene content. It applies more particularly to reforming effluents (post-fractionation or stabilization) or steam-cracking of naphthas (pre-fractionation).

The process of the invention can be generally defined by the fact that it combines two distillation stages with two permeation stages and that it comprises the following stages:

1) A mixture that contains benzene, other aromatic hydrocarbons and paraffinic hydrocarbons and/or naphthenic hydrocarbons that have 5 to 10 carbon atoms undergoes distillation in a first column, with said distillation producing a distillate and a residue;
2) a phase is drawn off laterally from said first distillation column, preferably at a point on the column where the benzene content is essentially at maximum and where the toluene content is low;
3) the phase that is drawn off is sent toward a first permeation stage, which produces a benzene-enriched permeate and a retentate;
4) at least a portion of said retentate, at at least one point on the latter, is recycled toward said first distillation column;
5) the concentrated permeate of stage (3) is sent to a second distillation column, from which the purified benzene comes out at the bottom and a distillate comes out at the top;
6) said distillate is condensed, and the condensed distillate is sent at least in part to a second permeation stage, with the remainder optionally being refluxed to the top of said second column;
7) in said second permeation stage, a permeate that is also enriched in benzene and a retentate are separated;
8) said permeate is sent back to said second distillation column; and
9) said retentate is recycled advantageously toward the inlet of the first permeation stage or directly toward the first distillation column.

As already indicated above, the first distillation column, in stage (1), can consist of a column for pre-fractionating a batch that consists of, for example, a naphtha, an effluent post-fractionating column of a reforming unit, or a reforming effluent stabilization column.

In the first case, the batch to be treated is generally a naphtha, which can contain, for example, 1 to 2% benzene. The distillation residue, which has little benzene and contains mainly $C_{7+}$ hydrocarbons, is used to feed the reforming unit. The distillate, which is also low in benzene and benzene precursors, such as cyclohexane and methylcyclopentane, can be subjected to a subsequent hydroisomerization treatment. The benzene content of the distillation depends on the specification of maximum benzene content of the residue that is fed to the reforming unit.

In the second case (post-fractionization), the reformate to be treated can contain, for example, about 5% benzene. The residue is very low in benzene and can be sent to a fuel pool. The distillate, which contains the remainder of the benzene that has not been removed by permeation, can undergo subsequent treatments, for example, hydroisomerization.

In these two cases, if the benzene content of the distillate does not exceed 3%, it can be isomerized without prior hydrogenation.

In the third case, the benzene is drawn off laterally at the stabilization column that is fed by the reforming effluent, and at the bottom of said column a residue is recovered that is low in benzene which generally is sent to the fuel pool or can undergo other treatments.

According to the principle of the process of the invention, the purification of benzene is done in stages (5) to (8), as they will be described later, without use of solvent but by using a new distillation and permeation operation. Actually, the benzene-enriched permeate that is obtained at the end of the first permeation stage feeds a second distillation column, whose bottom produces pure benzene and whose top feeds a second permeation unit. This second permeation unit produces a benzene-enriched permeate that feeds the distillation column and a retentate which is advantageously recycled to feed the first permeation unit.

BRIEF DESCRIPTION OF DRAWINGS

The process of the invention will be described in more detail below in connection with the schematic flowsheet of FIG. 1, which is given by way of illustration.

DETAILED DESCRIPTION OF DRAWINGS

Depending on its origin, the mixture of hydrocarbons to be treated can contain, for example, from 1 to 10% by mass of benzene.

In stage (1), the hydrocarbon batch to be treated comes in via line 1 into distillation column C1, which is generally operated at a pressure of 1 to 5 bars and is heated by a reboiler R1 so that the bottom temperature is 150 to 200° C. The top temperature is generally set at about 50° C. with a flow rate generally fixed at a value of 0.5 to 1 by mass relative to the column feed.

A vapor distillate that is cooled, for example, by passing into condenser E1, comes out at the top of column 1, via line 2 and is then sent into flask B1 via line 3. The condensed liquid phase is evacuated from flask B1 via line 5. A fraction of the latter is refluxed to the top of column C1 via line 7 and pump P1. The other fraction, which is evacuated via line 6, constitutes the clean distillate. In some cases, it is also possible to recover the clean distillate in vapor form, via line 4. At the bottom, a residue is collected via line 11.

In the case where column C1 is a post-fractionating column, the residue consists of a $C_{7+}$ fraction that is rich in aromatic $C_8$ compounds and contains a small proportion of benzene that was not sent to the fuel pool. The distillate that contains the remainder of the benzene, which was not removed by permeation, can be subjected to subsequent treatments such as hydroisomerization.

In stage (2), at least one point of column C1, at least one liquid phase, vapor phase or mixed phase, is drawn off laterally. The drawing-off is preferably done at a level of the column where the benzene concentration is at maximum or close to the maximum concentration and advantageously where the toluene concentration is low, preferably less than 100 ppm. The draw-off flow represents, for example, 30 to 70% of the flow of liquid phase or vapor phase that feeds the drawing-off tray. This flow generally represents 20 to 50% of the batch that feeds the column. The drawn-off phase is generally brought to a temperature of 60 to 120° C. in exchanger E2 and at a pressure such that it is at least partially liquid at the temperature in question, before being sent to the permeation unit; via line 8.

When the drawn-off phase in stage (2) is a liquid phase, the permeation technique used is more particularly a pervaporation. Furthermore, when the phase that is drawn off in stage (2) is a vapor phase or mixed phase, the permeation technique used is more particularly a vapor permeation.

In step (3), the permeation unit is fed by a lateral draw-off that is obtained from, as appropriate, the pre-fractionating column or post-fractionating column or the stabilization column. It produces a retentate that is low in benzene, which is sent to column C1 in stage (4), and a permeate whose benzene content can reach 90% by mass depending on the benzene selectivity of the membrane that is used and the concentration of benzene to feed the permeation unit.

The permeation unit is used in such a way that the benzene content of the top of the pre-fractionating column or post-fractionating column does not exceed 3% by mass and that about 50% of the benzene that is present in the batch is recovered in the permeate, a value that can vary depending on variations in the amount of benzene in the batch or the level of purification required of the benzene at the bottom of the column. The concentration factor, defined as the ratio between the concentration of benzene in the permeate to the concentration of benzene in the main feed to the fractionating column, is between 10 and 20.

In permeation device PV1 of stage (3), a membrane is generally used that has a benzene selectivity relative to aliphatic hydrocarbons of at least 6 and can go up to 15 or more.

It is possible to use various membranes that are known in the art. Many examples of membranes that are suited for separation by permeation of aliphatic and aromatic hydrocarbon mixtures are described in the prior art. Thus, U.S. Pat. No. 4,944,880 cites the use of materials such as chlorinated polyurethanes, polyimides/polyadipates, polyimides/polysuccinates to produce membranes that have good properties of permeability and selectivity, in particular to separate toluene/n-octane or iso-octane mixtures. To carry out this same separation, U.S. Pat. Nos. 4,997,906 and 5,019,666 respectively describe membranes that are produced from crosslinked copolymers of polyester diols and dianhydrides and membranes that are produced from crosslinked polycarbonates.

Other permeation membranes are described in the prior art: for example, oxazolidone/polyurea membranes in U.S. Pat. No. 5,039, 418 and various membranes of polyesters in U.S. Pat. Nos. 4,976, 868, 5,128,439 and 5,138,023.

Via line 9, permeation stage (3) produces a retentate that is low in benzene, which is picked up by pump P2 and sent back, in stage (4), partially or completely to laterally feed column C1 at at least one level of the latter. Thus, it can be advantageous to reintroduce the retentate at two levels, and more particularly at a level that is located above the feed of said column and at a level that is located below the latter.

If necessary, the retentate can be reheated or cooled in exchanger E3, before being reintroduced into the column. It is also possible to separate this retentate into a liquid phase and a vapor phase, in a flash flask, and to send back separately, partially or completely, one or two phases into said column.

Permeation stage (3) also produces, via line 10, a benzene-enriched vapor permeate, whose composition depends on the operating conditions of the process. The evacuated permeate of stage (3) is condensed at low pressure in heat exchanger E4, and is then picked up by pump P3 and sent to the subsequent purification stages.

In stage (5), the permeate, after being reheated in exchanger E6 up to a temperature of 80 to 120° C., feeds a second distillation column C2. Column C2 is generally used at a pressure of 1 to 2 bar and heated by a reboiler R2 in such a way that the bottom temperature is 80 to 120° C. The top temperature is generally set at about 70° C. with a reflux rate that is generally fixed at a value of 3 to 6 by mass relative to the supply of the column.

Via line 11, a vapor distillate comes out at the top of column C2 which, in stage (6), is cooled and condensed in exchanger E7, and then picked up by pump P5 and evacuated via line 13. This condensed distillate is at least in part sent into a second permeation device PV2, via line 15, in stage (7), with any remainder being refluxed to the top of column C2, via line 14.

In stage (5), a flux that contains benzene comes out at the bottom of column C2 via line 18 having purity levels that are required for its marketing.

Since the phase that is sent to permeation stage (7) is a liquid phase, the permeation technique that is used will be more particularly pervaporation.

In permeation device PV2 of stage (7), as in permeation device PV1, a membrane is generally used that has a benzene selectivity relative to aliphatic hydrocarbons of at least 6 and that can go up to 15 or more. Thus, it is possible to use various membranes that are known in the art, such as those already mentioned above for permeation stage (3).

The permeation operation of stage (7) produces, via line 17, a benzene-enriched vapor permeate, whose composition depends on the operating conditions of the process and generally varies between 70 and 95%. The permeate that is evacuated from permeation stage PV2 is condensed at low pressure in heat exchanger E5, then is picked up by pump P5, reheated by exchanger E, and is sent back at least partially to laterally feed column C2, in stage (8).

The permeation operation of stage (7) also produces, via line 16, a retentate that is low in benzene, which can be evacuated from the process but which, in a stage (9), is advantageously picked up by pump P4 and, depending on its concentration, sent back either to laterally feed column C1 at at least one point of the latter, or to feed permeation device PV1. If necessary, the retentate can be reheated or cooled in exchanger E8. It is also possible to separate this retentate into a liquid phase and a vapor phase, in a flash flask, and to send at least partially one or two phases back separately into said column C1 or into said permeation device PV1.

The advantages of the process of this invention over conventional techniques are:
  reduction in the operating costs associated with the purification of the benzene that is recovered during post-fractionation or pre-fractionation by permeation; and
  the ability to carry out fractionation with more flexibility: extracting a variable quantity of benzene according to market needs, the specification constraints of benzene content in fuels, and the variations of benzene content in the column feed.

The following example illustrates the invention without limiting it.

EXAMPLE

The treated batch is a reforming effluent that has the following composition:
  5.2% by weight of benzene
  17.8% by weight of toluene
  23.5% by weight of xylenes and ethyl benzene.

A post-fractionating column C1 that comprises 58 theoretical plates, at the level of the 36th plate computed from the condenser, is fed with this batch at a flow rate of 170 t/h.

A vapor distillate that is totally condensed at 58° C. and partially refeeds the column, with the liquid reflux rate relative to the feed being 0.7 by mass, is recovered at the top of the column. The distillate that is drawn off at the top contains 2.6% of benzene or 10.7% of the benzene fed.

In theoretical plate No. 20 of post-fractionating column C1, 32% of the liquid phase that feeds this tray is drawn off. The concentration of benzene of the liquid phase at this plate reaches 20.3% by mass, which is close to the maximum concentration of benzene in the column. The concentration of toluene of the liquid phase at this plate reaches 140 ppm by mass. This draw-off, at 107° C., is sent to a pervaporation unit PV1 that comprises a pervaporation membrane of 3200 $m^2$ whose benzene selectivity relative to aliphatic hydrocarbons is about 10. This membrane was synthesized from a mixture of polyimide and polysuccinate according to the description of Example 7 of U.S. Pat. No. 4,944,880.

A proportion of 50% of benzene that is contained in the draw-off is evacuated by pervaporation in the permeate, whose benzene concentration is set at 72% by mass.

The retentate, which contains no more than 11.9% of benzene, is separated into two fractions, with one feeding column C1 in stage No. 21 and the other feeding column C1 in stage No. 50. In this way, it is possible, while keeping a low content of benzene in the distillate (2.5% by mass), to obtain a residue that does not contain more than 2.7% of benzene.

After condensation, the permeate that is derived from the pervaporation unit is pumped and reheated up to a temperature of 86° C., and then sent into a second fractionating column C2 at theoretical plate No. 7.

A vapor distillate, which is totally condensed at 73° C. and which partially refeeds the column, with the liquid reflux rate relative to the supply being 5.3 by mass, is removed at the top of column C2. The distillate that is drawn off at the top contains 55% benzene.

The fraction of the liquid distillate that is not refluxed on column C2 feeds a second pervaporation unit PV2 that comprises a pervaporation membrane of 1100 $m^2$ whose benzene selectivity relative to aliphatic hydrocarbons is about 10. This membrane is of the same type that is used in pervaporation device PV1 described above.

A proportion of 80% of the benzene that is contained in the feed is evacuated by pervaporation into the permeate, whose benzene concentration is set at 89% by mass. After condensation, this permeate is pumped, reheated and sent in lateral feed to column C2 at theoretical stage No. 7.

The retentate that is obtained from pervaporation unit PV2 and that does not contain more than 22% by mass of benzene is pumped and reheated up to a temperature of 103° C., and then mixed with lateral draw-off that is obtained from post-fractionating column C1 and that feeds pervaporation unit PV1.

Fractionating column C2 is reboiled at the bottom at a temperature of 104° C. A residue that contains 99.9% by mass of benzene is thus obtained.

The preceding examples can be repeated with similar success by substituting the generically or specifically described reactants and/or operating conditions of this invention for those used in the preceding examples.

The entire disclosure of all applications, patents and publications, cited above and below, and of corresponding French application 96/11695, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for obtaining high-purity benzene from a mixture that contains benzene, other aromatic hydrocarbons and paraffinic and/or naphthenic hydrocarbons that have 5 to 10 carbon atoms, comprising the following numerically identified stages:

1) distilling the mixture of hydrocarbons in a first column, with said distillation producing a distillate and a residue;
   2) drawing off a phase laterally from said first distillation column,
   3) passing the drawn-off phase toward a first permeation stage, which produces a benzene-enriched permeate and a retentate;
   4) recycling at least a portion of said retentate, to said first distillation column;
   5) passing the benzene-enriched permeate from stage (3), to a second distillation column, from which the purified benzene comes out at the bottom and a distillate vapor comes out at the top;
   6) condensing said distillate vapor, and sending the condensed distillate at least in part to a second permeation stage;
   7) in said second permeation stage, separating the condensed distillate into a permeate that is also enriched in benzene and a retentate; and
   8) recycling said permeate from stage 7 to said second distillation column.

2. A process according to claim 1, wherein in stage (1), said first distillation column is used at a pressure of 1 to 5 bar and at a bottom temperature of 150 to 200° C., with the top temperature being set at about 50° C. with a reflux rate set at a value of 0.5 to 1 by mass relative to the feed of the column.

3. A process according to claim 1, wherein in stage (2), drawing-off is done at a level of the column where the benzene concentration is essentially at a maximum.

4. A process according to claim 3, wherein said drawing-off is carried out at a level of the column where the toluene concentration is less than 100 ppm.

5. A process according to claim 1, wherein the phase that is drawn off in stage (2) is brought to a temperature of 60° to 120° C. and at a sufficient pressure to form an at least partially liquid phase.

6. A process according to claim 1, wherein in stage (2), the draw-off flow represents 20 to 50% by mass of the mixture that feeds the column.

7. A process according to claim 1, wherein the phase that is drawn off in stage (2) is a liquid phase, a vapor phase, or a mixed phase.

8. A process according to claim 1, wherein the phase that is drawn off in stage (2) comprises a liquid phase and wherein the permeation stage (3) comprises pervaporation of said liquid phase.

9. A process according to claim 1, wherein the phase that is drawn off in stage (2) is a vapor phase or a mixed phase and wherein the permeation stage (3) comprises vapor permeation of said vapor.

10. A process according to claim 1, wherein in first permeation stage (3), the permeation is conducted through a membrane having a benzene selectivity relative to other components of at least 6.

11. A process according to claim 10, wherein in permeation stage (3), the membrane comprises a chlorinated polyurethane, a polyimide/polyadipate, a polyimide/polysuccinate, a crosslinked copolymer of polyester diol and dianhydride or a crosslinked polycarbonate.

12. A process according to claim 1, wherein in stage (4), the retentate is sent back at two separate levels of said first column.

13. A process according to claim 12, wherein the first distillation column has a feedpoint and one of said levels is located above the feed point to said column and the other is located below the feedpoint.

14. A process according to claim 1, wherein in stage (6), the condensed distillate is sent back in part to the top of said second column, as reflux.

15. A process according to claim 1, wherein permeation stage (7) comprises pervaporation.

16. A process according to claim 1, wherein in second permeation stage (7), the permeation is conduced through a membrane having a benzene selectivity relative to the other components of at least 6.

17. A process according to claim 16, wherein the membrane used in permeation stage (7) comprises a chlorinated polyurethane, a polyimide/polyadipate, and polyimide/polysuccinate, a crosslinked copolymer of polyester diol and dianhydride, or a crosslinked polycarbonate.

18. A process according to claim 1, wherein said retentate of the second permeation stage obtained in stage (7) is sent back, in additional stage (9), to the first distillation column.

19. A process according to claim 1, wherein said retentate of the second permeation stage that is obtained in stage (7) is sent back, in additional stage (9), to the input of the first permeation stage.

20. A process according to claim 1, wherein the mixture to be treated is a naphtha and the first distillation column is a pre-fractionation column.

21. A process according to claim 1, wherein the mixture to be treated is a reformate and the first distillation column is a post-fractionation column.

22. A process according to claim 21, wherein said retentate from the second permeation stage (7) is sent back, in an additional stage (9), to the feed of the first distillation column.

23. A process according to claim 21, wherein said retentate from the second permeation stage (7) is sent back, in an additional stage (9), to the inlet of the first permeation stage (3).

24. A process according to claim 1, wherein the mixture to be treated is a reformate and the first distillation column is a stabilization column.

* * * * *